United States Patent
McLaughlin et al.

(10) Patent No.: US 10,159,581 B2
(45) Date of Patent: *Dec. 25, 2018

(54) EXPANDABLE VERTEBRAL IMPLANT

(71) Applicant: GLOBUS MEDICAL, INC., Audubon, PA (US)

(72) Inventors: Colm McLaughlin, Glenside, PA (US); James Himmelberger, Souderton, PA (US)

(73) Assignee: Globus Medical, Inc., Audubon, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/810,858

(22) Filed: Nov. 13, 2017

(65) Prior Publication Data

US 2018/0078382 A1    Mar. 22, 2018

Related U.S. Application Data

(63) Continuation of application No. 15/147,363, filed on May 5, 2016, now Pat. No. 9,844,446.

(51) Int. Cl.
  *A61F 2/44* (2006.01)
  *A61F 2/46* (2006.01)
(52) U.S. Cl.
  CPC .............. *A61F 2/446* (2013.01); *A61F 2/44* (2013.01); *A61F 2/4611* (2013.01); *A61F 2002/4475* (2013.01); *A61F 2002/4615* (2013.01)

(58) Field of Classification Search
  CPC .......... A61F 2/44; A61F 2/446; A61F 2/4611; A61F 2002/4475; A61F 2002/4615
  USPC ................. 606/246; 623/17.11, 17.15, 17.16
  See application file for complete search history.

(56) References Cited

U.S. PATENT DOCUMENTS

| | | |
|---|---|---|
| 6,176,881 B1 | 1/2001 | Shar et al. |
| 6,524,341 B2 | 2/2003 | Lang et al. |
| 6,730,088 B2 | 5/2004 | Yeh |
| 6,866,682 B1 | 3/2005 | An et al. |
| 6,899,734 B2 | 5/2005 | Castro et al. |
| 6,908,485 B2 | 6/2005 | Crozet et al. |
| 6,929,662 B1 | 8/2005 | Messerli et al. |
| 7,156,874 B2 | 1/2007 | Paponneau et al. |
| 7,303,584 B2 | 12/2007 | Castro et al. |
| 7,311,733 B2 | 12/2007 | Metz-Stavenhagen |
| 7,544,208 B1 | 6/2009 | Mueller et al. |
| 7,575,601 B2 | 8/2009 | Dickson |
| 7,648,529 B2 | 1/2010 | An et al. |

(Continued)

*Primary Examiner* — Pedro Philogene
*Assistant Examiner* — David C Comstock

(57) ABSTRACT

An expandable prosthetic implant for engagement between vertebrae includes a first member having a first end, a second end, a plurality of extensions and and a hollow interior portion extending from the first end to the second end, wherein the plurality of extensions extend from the first end to the second end. A second member includes a first end, a second end, a hollow interior portion extending from the first end to the second end, and a plurality of extensions extending from the second end to the first end. The plurality extensions of the first member are configured to coaxially interdigitate with the second member, and the plurality of extensions of the second member are configured to coaxially interdigitate with the first member. The first member of the implant is moveable relative to the second member along a longitudinal axis.

20 Claims, 10 Drawing Sheets

(56) References Cited

U.S. PATENT DOCUMENTS

| | | |
|---|---|---|
| 7,758,648 B2 | 7/2010 | Castleman et al. |
| 7,819,920 B2 | 10/2010 | Assaker |
| 7,879,096 B2 | 2/2011 | Dickson et al. |
| 7,909,870 B2 | 3/2011 | Kraus |
| 7,914,581 B2 | 3/2011 | Dickson et al. |
| 8,034,111 B2 | 10/2011 | Hsu et al. |
| 8,057,545 B2 | 11/2011 | Hughes et al. |
| 8,062,366 B2 | 11/2011 | Melkent |
| 8,182,535 B2 | 5/2012 | Kraus |
| 8,197,546 B2 | 6/2012 | Doubler et al. |
| 8,252,054 B2 | 8/2012 | Greenhalgh et al. |
| 8,268,004 B2 | 9/2012 | Castleman et al. |
| 8,282,683 B2 | 10/2012 | McLaughlin et al. |
| 8,353,961 B2 | 1/2013 | McClintock et al. |
| 8,366,779 B2 | 2/2013 | Dickson et al. |
| 8,372,151 B2 | 2/2013 | Hsu et al. |
| 8,585,763 B2 | 11/2013 | Olevsky et al. |
| 8,591,585 B2 | 11/2013 | McLaughlin |
| 8,657,882 B2 | 2/2014 | Bonin, Jr. |
| 8,663,330 B2 | 3/2014 | McClintock et al. |
| 8,721,723 B2 | 5/2014 | Hansell et al. |
| 8,870,880 B2 | 10/2014 | Himmelberger |
| 8,882,840 B2 | 11/2014 | McClintock et al. |
| 9,009,927 B2 | 4/2015 | Rigollet et al. |
| 9,173,747 B2 | 11/2015 | Hansell et al. |
| 9,180,018 B2 | 11/2015 | Hansell et al. |
| 9,271,842 B2 | 3/2016 | Davenport et al. |
| 9,301,850 B2 | 4/2016 | McLaughlin et al. |
| 9,844,446 B2 * | 12/2017 | McLaughlin ........... A61F 2/446 |
| 2008/0167720 A1 | 7/2008 | Melkent |
| 2013/0197648 A1 | 8/2013 | Boehm et al. |

\* cited by examiner

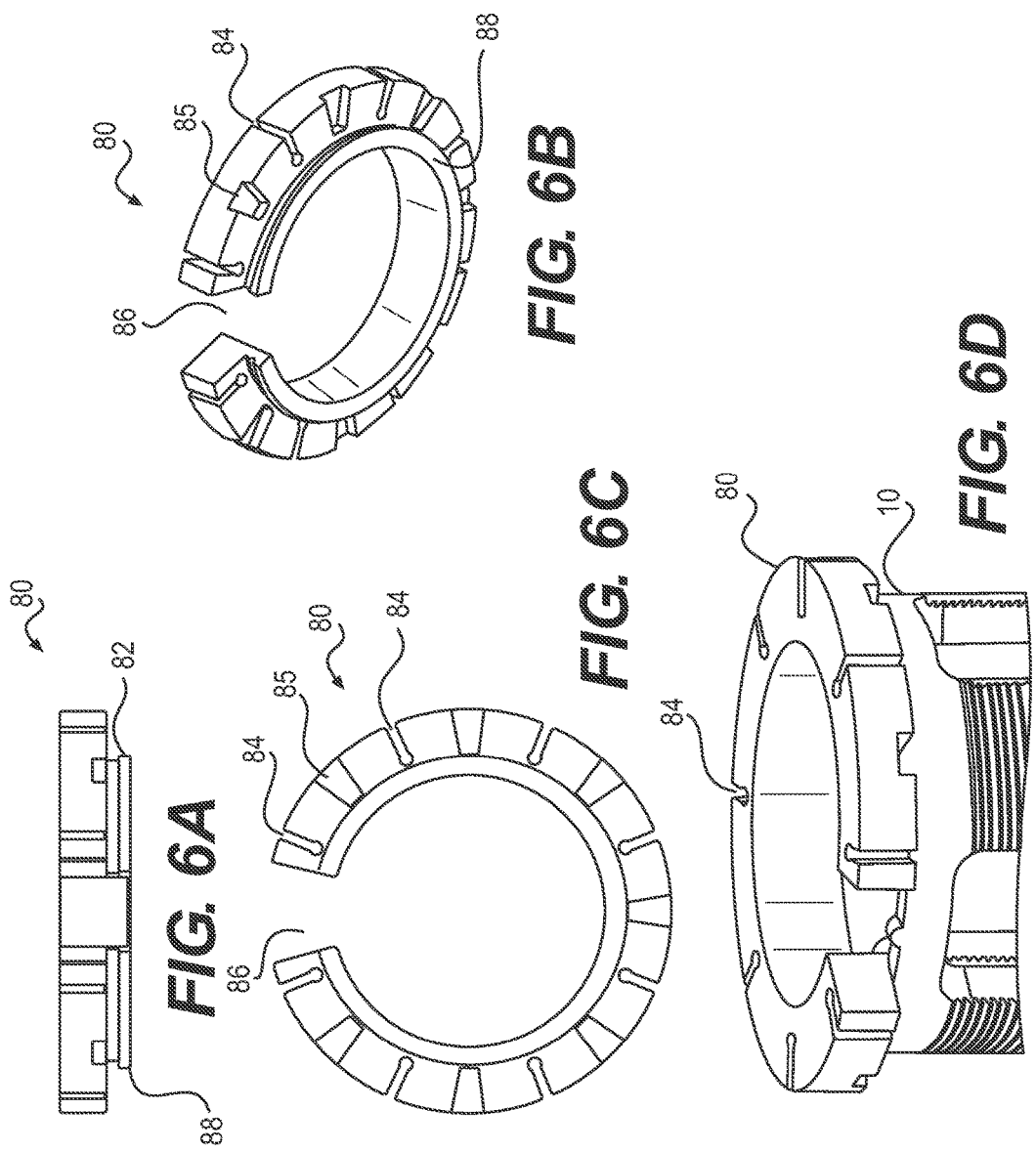

EXPANDABLE VERTEBRAL IMPLANT

CROSS-REFERENCE TO RELATED APPLICATIONS

This application is a continuation of U.S. patent application Ser. No. 15/147,363 filed on May 5, 2016, which is incorporated in its entirety herein.

FIELD OF THE INVENTION

The present invention relates to a device to support the spine after removal of at least a part of a vertebra. In particular, the device may be in the form of a multi-level implant which can replace multiple vertebral bodies.

BACKGROUND OF THE INVENTION

When a vertebra is damaged or diseased, surgery may be used to replace the vertebra or a portion thereof with a prosthetic device to restore spinal column support. For example, vertebral body replacement is commonly required in the treatment of vertebral fracture, tumor, or infection.

In recent years, several artificial materials and implants have been developed to replace the vertebral body, such as, for example, titanium cages, ceramic, ceramic/glass, plastic or PEEK, and carbon fiber spacers. Recently, various expandable prosthetics or expandable cages have been developed and used for vertebral body replacement. The expandable prosthetic devices are generally adjustable to the size of the cavity created by a corpectomy procedure and typically are at least partially hollow to accommodate bone cement or bone fragments to facilitate fusion in vivo. Some expandable implants may be adjusted prior to insertion into the cavity, while others may be adjusted in situ. Two advantages of the vertebral body replacement using an expandable prosthetic device that is adjustable in situ is that it is easy to place or insert and it permits an optimal, tight fit by in vivo expansion of the device. Some other advantages offered by an expandable prosthetic device are that they can facilitate distraction across the resected vertebral defect and allow immediate load bearing after a corpectomy procedure.

Instrumentation and specialized tools for insertion of a vertebral implant is one important design parameter to consider when designing a vertebral implant. Spinal surgery procedures can present several challenges because of the small clearances around the prosthetic when it is being inserted into position. Another important design consideration includes the ability of the device to accommodate various surgical approaches for insertion of the vertebral implant and considerations in positioning the device within differing anatomical structures.

SUMMARY OF THE INVENTION

According to one embodiment, an expandable prosthetic implant for engagement between vertebrae includes a first member having a first end, a second end, a plurality of extensions and and a hollow interior portion extending from the first end to the second end, wherein the plurality of extensions extend from the first end to the second end. A second member includes a first end, a second end, a hollow interior portion extending from the first end to the second end, and a plurality of extensions extending from the second end to the first end. The plurality extensions of the first member are configured to coaxially interdigitate with the second member, and the plurality of extensions of the second member are configured to coaxially interdigitate with the first member. The first member of the implant is moveable relative to the second member along a longitudinal axis.

In one embodiment, a ring is positioned coaxial to the first member and the second member and axially fixed to the second member. An actuator is coupled to the second member and operationally coupled to the ring for locking the first member to the second member.

In one embodiment, at least one of the plurality of extension of the first member includes engagement features that engage with the corresponding engagement element on an inner surface of the ring. In a first position, the first member is freely moveable in the longitudinal axis with respect to the second member. When the ring is moved from the first position to a second position by rotation of the actuator through the use of an instrument, the first member is locked in a position with respect to the second member.

BRIEF DESCRIPTION OF THE DRAWINGS

The present invention will be more readily understood with reference to the embodiments thereof illustrated in the attached drawing figures, in which:

FIGS. 6A-6D illustrate one embodiment of an endplate used with an expandable implant;

Throughout the drawing figures, it should be understood that like numerals refer to like features and structures.

DETAILED DESCRIPTION OF THE INVENTION

The preferred embodiments of the invention will now be described with reference to the attached drawing figures. The following detailed description of the invention is not intended to be illustrative of all embodiments. In describing preferred embodiments of the present invention, specific terminology is employed for the sake of clarity. However, the invention is not intended to be limited to the specific terminology so selected. It is to be understood that each specific element includes all technical equivalents that operate in a similar manner to accomplish a similar purpose. The features of one embodiment may be employed with other embodiments as the skilled artisan would recognize, even if not explicitly stated herein.

Figure 1:
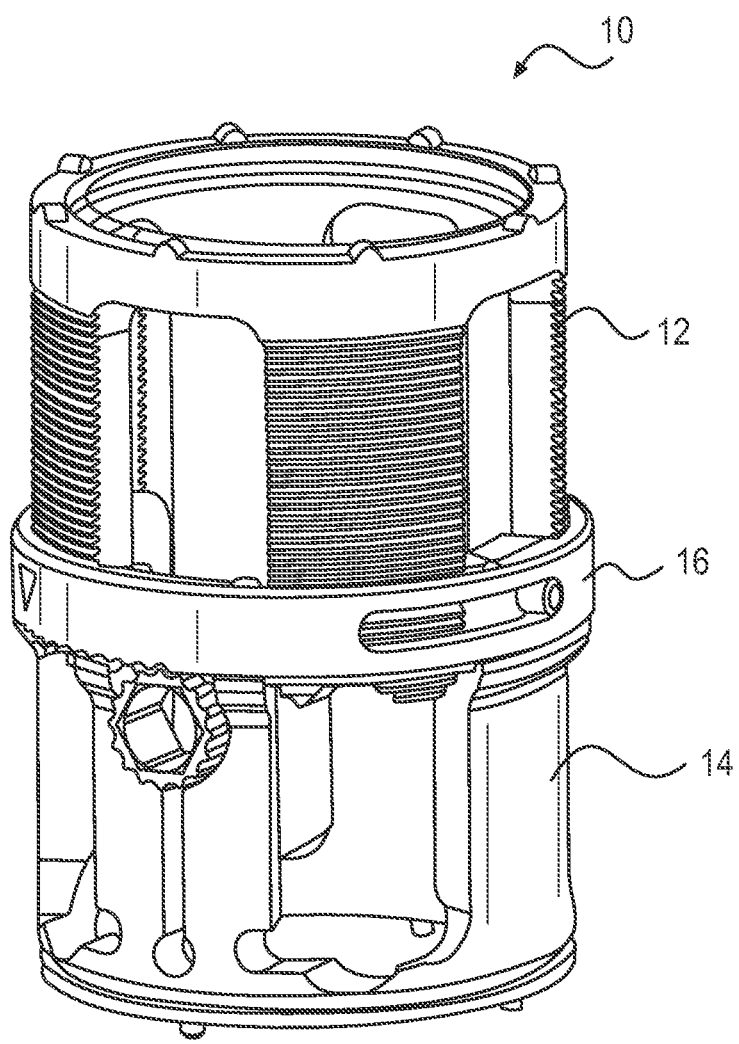
FIG. 1 is a perspective view of an implant in accordance with an embodiment of the present invention.
Figure 2:
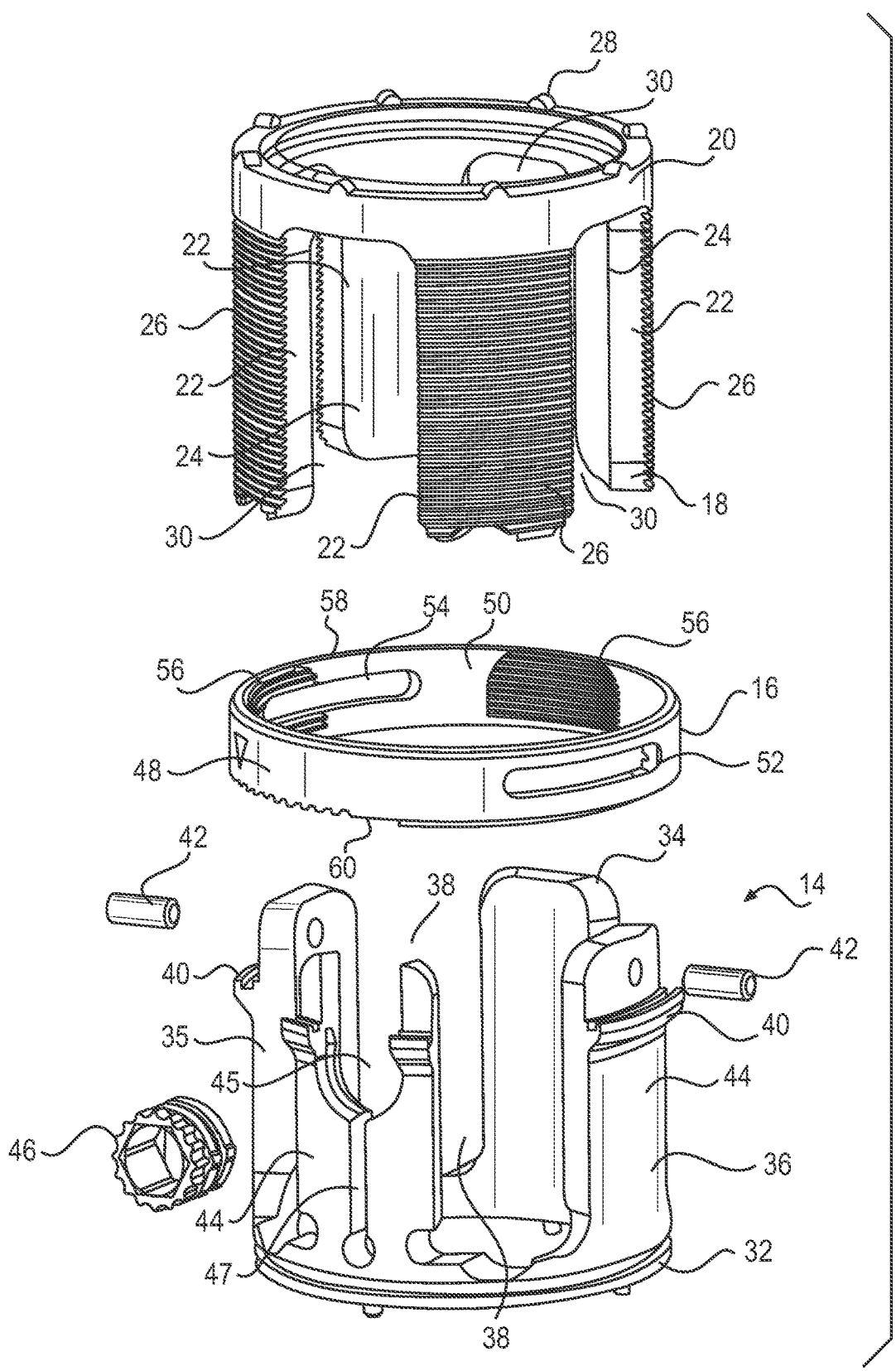
FIG. 2 is an exploded view of the implant of FIG. 1.
Figure 3:
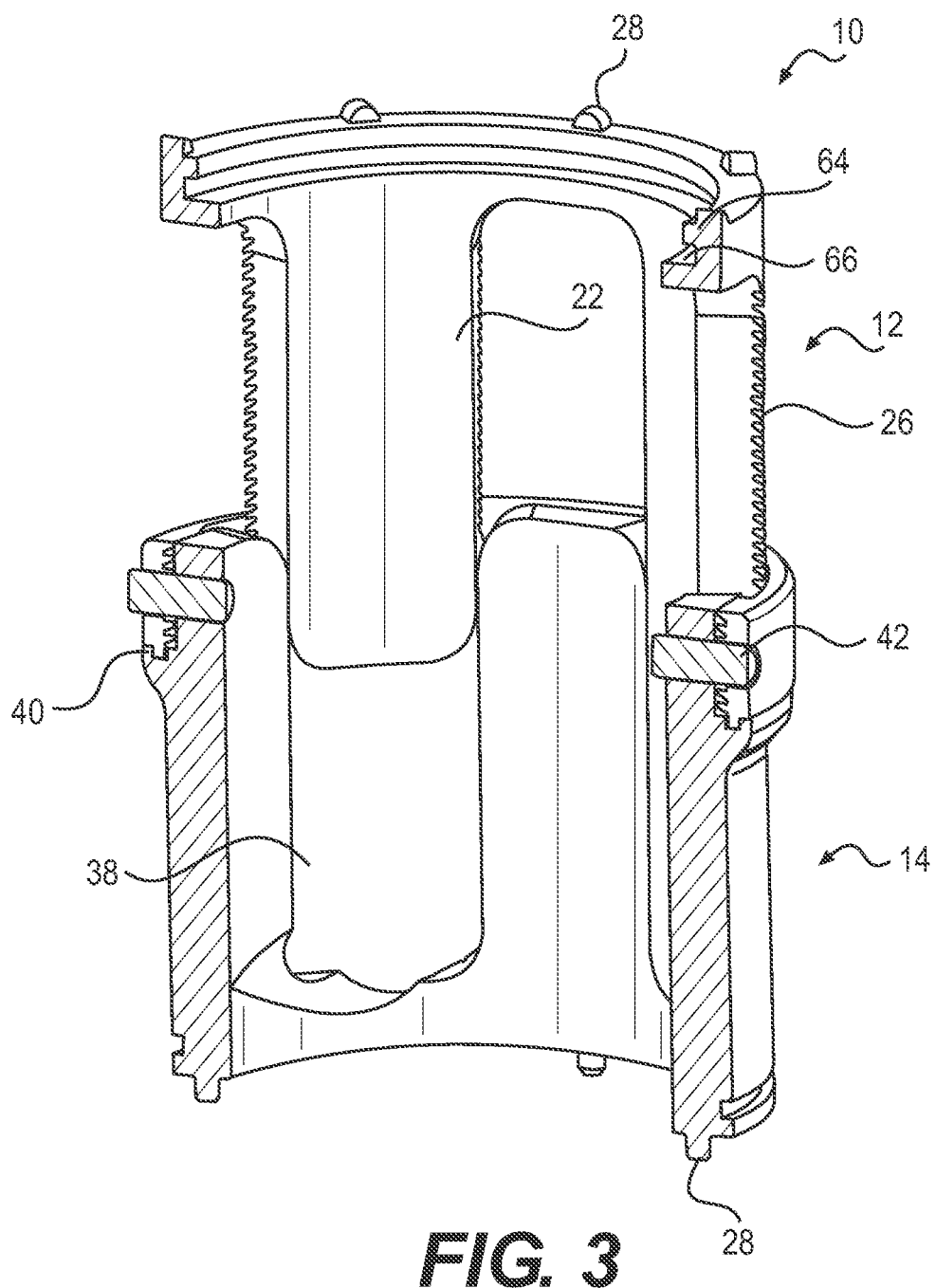
FIG. 3 is a cross-sectional view of the implant of FIG. 1.

Referring to FIGS. 1-3, a preferred embodiment of an expandable vertebral implant 10 is shown. The implant 10 preferably comprises a first member 12 which may be operationally coupled with a second member 14. The first member 12 and the second member 14 are configured to interdigitate with one another, and will be discussed in greater detail below. To achieve expansion or contraction of the implant 10, a distractor type instrument is used to move the first member 12 with respect to the second member 14. The implant 10 further comprises a ring 16 that is used to lock and unlock the first member 12 with respect to the second member 14. The first member 12, the second member 14, and the ring 16 are preferably centered along a longitudinal axis and define a hollow interior portion which may be filled with bone material, bone growth factors, bone morphogenic proteins, or other materials for encouraging bone growth, blood vessel growth or growth of other tissue through the many apertures in the device. In one preferred embodiment, members 12, 14, and 16 are made of a polyether ether ketone (PEEK) plastic material. There are several known advantages of PEEK plastic material including being radiolucent, having a mechanical strength that is close to bone, and may be more easily sterilized than other plastics. In alternate preferred embodiments, the members 12, 14, and 16 may be made of a biologically inert metal alloys, such as titanium, or other suitable materials.

Referring to FIGS. 1-3, the first member 12 has a generally cylindrical body with a distal end 18 and a proximal end 20. In a preferred embodiment, the first member 12 includes a plurality of extensions 22 extending form the proximal end 20 to the distal end 18. The plurality of extensions 22 having an inner surface 24, an outer surface 26, and side surfaces. The plurality of extensions 22 are spaced from one another. In one embodiment, the outer surfaces 26 of the plurality of extensions 22 may have engagement features. The engagement features may be a plurality of concentric teeth, non-helical threads, ratchet type features, tabs (flexible and non-flexible) and other similar mechanical elements. On an upper surface at the proximal end 20 of the first member 12 in one embodiment there are provided a plurality of endplate engagement features 28. Endplate engagement features 28 are adapted to engage with an endplate. The endplate engagement features 28 as more clearly illustrated in FIG. 3 may be tabs, fingers, extensions, or in one embodiment arcuate tabs that engage with a corresponding mating feature of the endplate. As the plurality of extensions 22 are spaced apart from one another, there are a plurality of openings between the plurality of extensions 22.

The second member 14 has a generally cylindrical body with a distal end 32 and a proximal end 34. In preferred embodiment, the second member 14 includes a plurality of extensions 36 and a plurality of openings 38 positioned between the plurality of extensions 44. The plurality of extensions 36 of the second member includes an inner surface, an outer surface, and side surfaces. The outer surface of the plurality of extensions 36 include a mating feature 40 configured to be coupled with the ring 16. It should be noted that the mating feature 40 may be any feature that clamps, locks, holds, or secures the ring 16 to the second member 14. In one embodiment, the mating feature is a ledge type feature. The plurality of extensions may also be provided with at least two openings extending from the outer surface to the inner surface of the extensions. Pins 42 may be used to lock the ring 16 to the second member 14. In the preferred embodiment, the ring 16 is positioned within the mating feature 40, and locked to the second member 14 by pins 42.

In a preferred embodiment, at least one of the plurality of extensions 44 of the second member 14 includes an opening 45 for receiving an actuator 46 for actuating the ring 16. The extension 44 further includes a slot 47 that extends from the opening 45 towards the distal end 32 of the second member 14. In a preferred embodiment, the slot 47 is provided so that the extension 44 may be compressible and/or flexible. In other embodiments the extension 44 may not be fixed and not compressible and/or flexible. The opening 45 of the extension 44 may have perimeter that has a radius or in other embodiments may be linear. In the preferred embodiment, the internal surfaces of the extension 44 have a radius and are manufacture to be able to receive and secure the actuator 46. The internal surfaces of the extension 44 include elements that allow for the securing the actuator 46, such as tabs, divots, protrusions that correspond to features provided on the actuator 46.

The plurality of extensions of the first member and second member may be designed in any geometrical shape for allowing for interdigitating with either first or second members. For instance, the plurality of extensions may be in the shape of a cylinder, pyramid, oblong, and other suitable variation. Preferably, the first member and the second member configured to interdigitate such that one of the first and second members is not received inside the other of the first and second members, for example, in a telescoping fashion. In other words, the outer diameter of both the first and second members may be substantially identical or the same. Although the preferred embodiment illustrates the first member and the second member configured to interdigitate, in the alternative, it is envisioned that the first member and the second member may be configured to be telescopingly coupled to one another. For instance, in some embodiments the first member 12 may be positioned within the internal surface of the second member. During operation, an instrument or any other suitable mechanism may be used to expand the first member 12 relative to the second member 14. In other embodiments, the second member may be telescoping relative to the first member 12. In these embodiments, the second member 14 is positioned within the internal surfaces of the first member 12.

The actuator 44 is a cylindrical body having an outer surface and an inner surface. The outer surface of the actuator 44 includes an instrument engaging surface such a hex shaped groove for receiving a corresponding instrument. Although a hex shaped surface is illustrated in the FIGS. It should be noted that any instrument engaging surface that receives a corresponding feature from an instrument may be used to operate the actuator 46. In the perimeter of the actuator 46 there are provided rounded teeth for engaging with the actuation features of the ring 16. The actuator 46 also includes protrusions that engage with a groove within the inner surfaces of the extension 44. The actuator 46 can be rotated within the opening 45, as the protrusions are configured to move within the groove.

The distal end 32 of the second member 14 also includes endplate engagement features 28. These engagement features 28 are configured to couple to the second endplate. The endplate engagement features 28 may be tabs, fingers, extensions, or in one embodiment arcuate tabs that engage with a corresponding mating feature of an endplate.

The ring 16 is configured to lock the first member 12 to the second member 14. The ring 16 has an outer surface 48 and an inner surface 50. The ring 16 also includes a first slot 52 and a second slot 54 positioned on opposing sides. On the inner surface 50 of the ring are engagement features 56 that correspond to the engagement features 26 of the first member 12. The ring 16 is positioned within the mating feature 40 of the second member 14 and locked via pins 42. Pins 42 extend though openings in the extensions of the second member 14 into the first and second slots 52, and 54. The ring 16 also includes an upper surface 58 and a lower surface 60. The lower surface 60 of the ring has actuation features 62 for allowing the actuation of the ring 16. The actuation features 62 engage with the rounded teeth of the actuator 46. When the actuator is moved, rounded teeth engage with the actuation features 62 and causes the the ring 16 to be turned. As a result, the engagement features 56 of the ring may align with the engagement features 26 of the first member thereby locking the first member 12 to the second member 14. In a preferred embodiment, ring 16 is rotated 45 degrees so that the engagement features 56 of the ring 16 engage with the engagement features 26 of the first member 12.

The first member 12 and the second member 14 are configured so that the first and second members interdigitate with one another. In the preferred embodiment, the plurality of extensions 26 of the first member 12 are positioned within the plurality of openings 38 in the second member. And the plurality of extensions 36 of the second member 14 are positioned within the plurality of openings 30 in the first member in an unexpanded state. The first member 12 is configured to be engaged with an instrument that translates the first member 12 in the longitudinal axis, thereby expanding the implant. Once the selected amount of expansion is reached, the ring 16 is rotated via the actuator 46 which locks the first member 12 relative to the second member 14.

Figure 5:
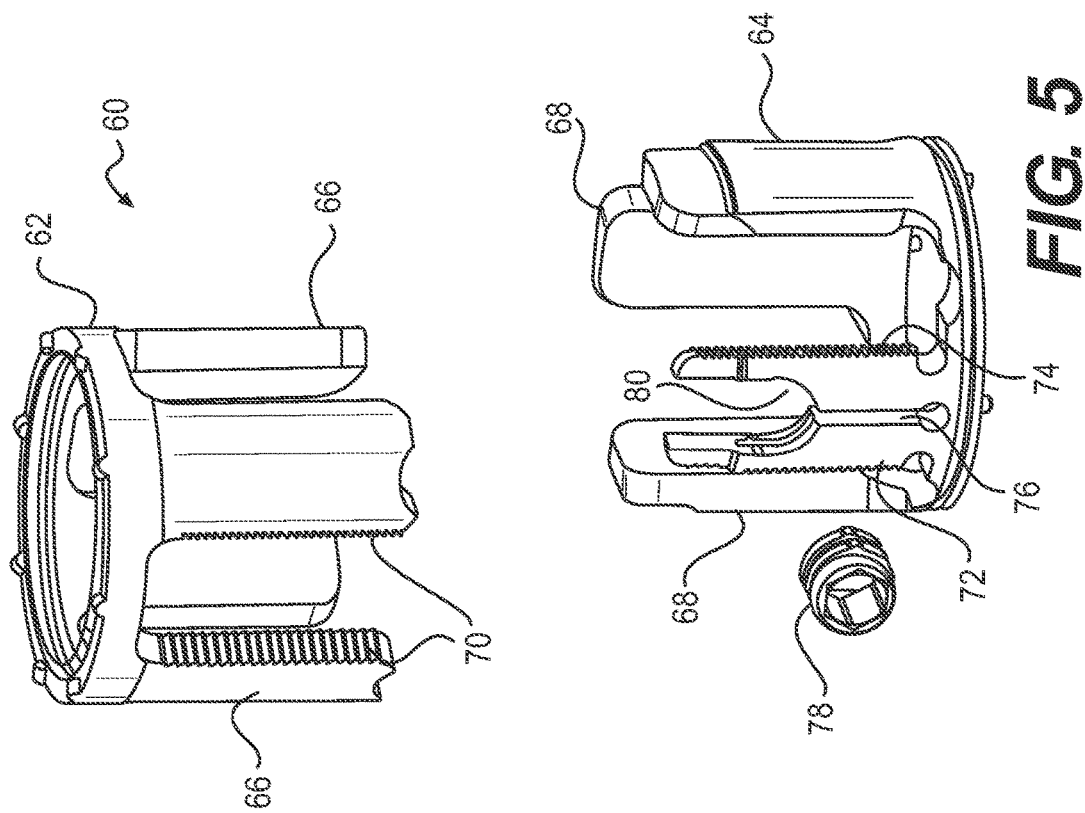
FIG. 5 is an exploded view of implant of FIG. 4.
Figure 4:
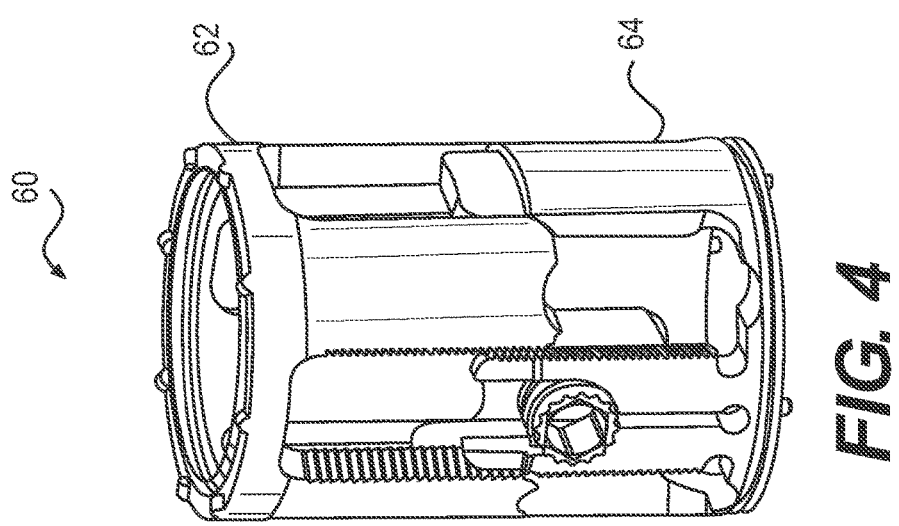
FIG. 4 is perspective view of of another embodiment of an expandable implant.

FIGS. 4 and 5 illustrate another embodiment of an expandable implant. FIGS. 4 and 5 illustrate an implant 60 having a first member 62 and a second member 64. The first and second members 62, 64 are adapted to correspondingly mate with one another. The first member 62 includes a plurality of extensions 66 extending from a first end towards a second end. The second member 64 includes a plurality of extensions 68 extending from a first end to a second end. The first and second members 62, 64 also include a plurality of openings for receiving the plurality of extensions 66, 68 thereby interdigitating with one another. At least two of the extensions 66 of the first member include inner side surfaces 70 that have engagement features such as ledges, non-helical threads, and/or ratchet style teeth. At least one extension 72 of the second member 64 has outer side surfaces 74 that have corresponding engagement features that engage with the engagement features on the side surfaces of the at least two extensions 66 of the first member 62. The extension 72 of the second member also includes a slot 76 extending from the first end towards the second end. The extension 72 of the second member is configured to be compressible when an actuator element 78 is rotated within a housing 80.

The actuator 78 is a cylindrical body having an outer surface and an inner surface. The outer surface of the actuator 78 includes an instrument engaging surface such a hex shaped groove for receiving a corresponding instrument. Although a hex shaped surface is illustrated in the FIGS, it should be noted that any instrument engaging surface that receives a corresponding feature from an instrument may be used to operate the actuator 78. The actuator 78 also includes protrusions that engage with a groove within the inner surfaces of the extension 72. The actuator 78 can be rotated within the housing 80, as the protrusions are configured to move within the groove. In first position, the first member and the second member are not engaged and as a result, the first member is moveable with respect to the second member. In a second position, the first member is locked to the second member when the actuator is rotated and the protrusion within the groove cause the extension 72 to flex out. When the extension flexes out the side surfaces of the legs 82, 84 engage with the engagement features of extension 70 of the first member.

The benefit provided by the present locking mechanism provided in the above embodiments is that it allows for a positive lock that engages and disengages automatically with the engagement and disengagement of the tool with the implant 10, which minimizes the steps the surgeon must perform during the procedure.

Referring now to FIGS. 6A-6D, in a preferred embodiment, an endplate 80 is shown wherein the endplate 80 connects to the first member 12 or second member 14 of an expandable implant 10. Although a single endplate 80 is illustrated, it should be noted that a second endplate may be coupled to the second member 14 and has similar characteristics of the described endplate 80. In a preferred embodiment, each endplate 80 is generally annular in shape when viewed from the end or perpendicular to the longitudinal axis. It is, however, contemplated that the endplates 80 can be other shapes including oblong, elliptical, kidney bean, polygonal, or geometric. Preferably, the endplates 80 may be designed to resemble or mimic the footprint of the vertebral body to which the endplates will engage. In this regard, endplates 80 are configured to engage portions of the vertebrae in a predetermined orientation to maximize contact of the superior surface of the endplates 80 with bone.

As shown in FIGS. 6B and 6C, in a preferred embodiment, the endplate 80 includes an extension 82, and a plurality of slots 84 spaced around the perimeter of the endplate 80. The plurality of slots 84 and an opening 86 in the perimeter of the endplate 80 allows the endplate 80 to be compressible. The endplate 80 being compressible facilitates the coupling of the endplate 80 with either the first member 12 or second member 14 of the expandable implant 10. In other embodiments, the endplate 80 may include cutouts 85 for receiving the engagement features 28 of the first and second member 12, 14.

Figure 7A:
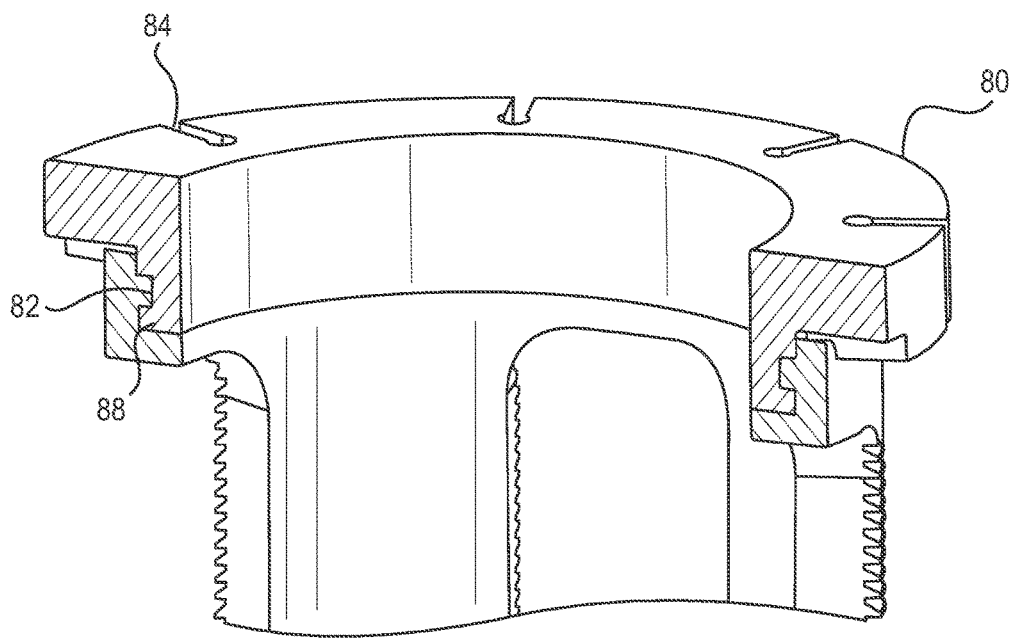
FIGS. 7A and 7B illustrate cut-out views of the endplate of FIGS. 6A-6D coupled to an expandable implant.
Figure 7B:
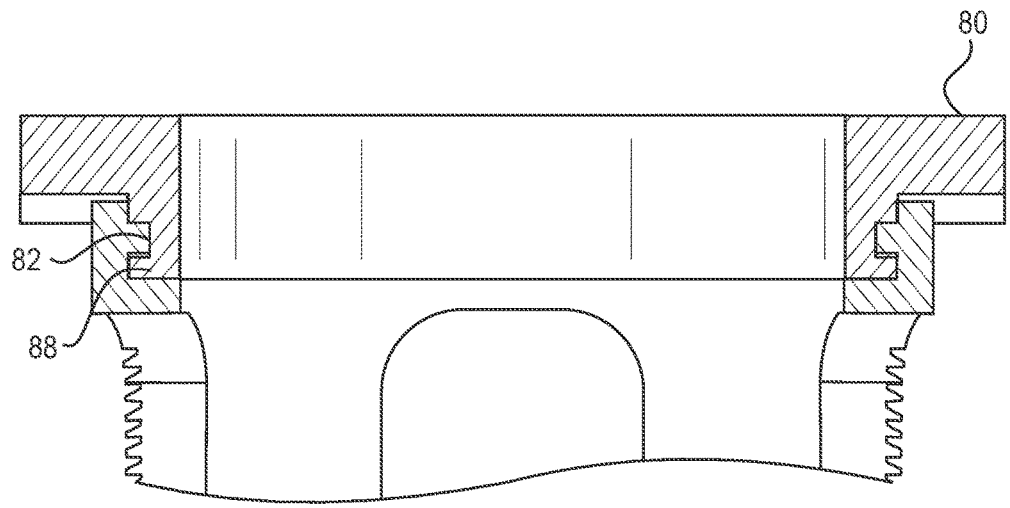
Figure 8A:
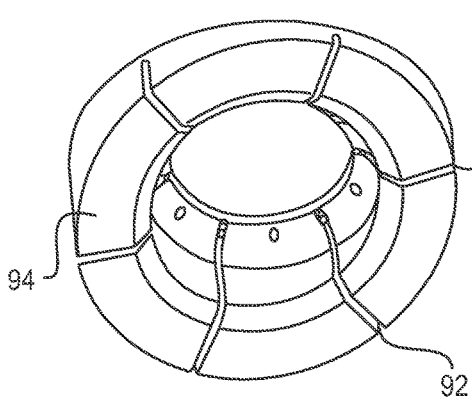
FIGS. 8A-8D illustrate another embodiment of an endplate.
Figure 8B:
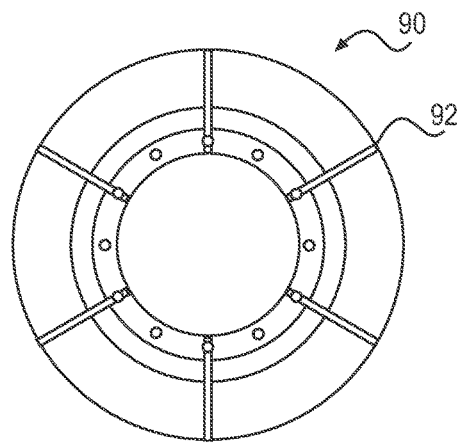
Figure 8C:
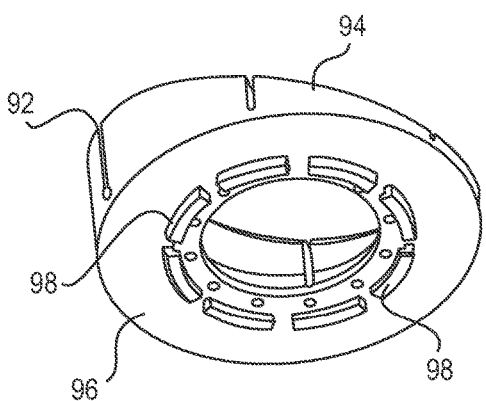
Figure 8D:
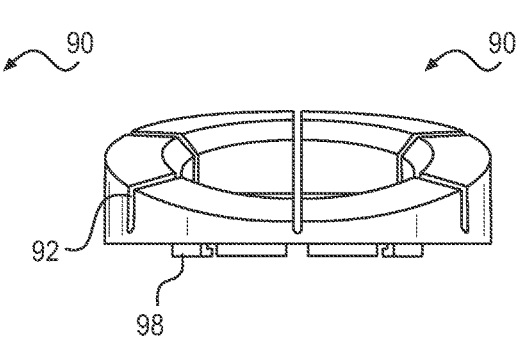

In a preferred embodiment, the extension 82 extends from a bottom surface of the endplate 80 and is configured with rim 88 that extends around the perimeter of the extension 82. The extension 82 is also configured to be mate with the first and second members 12, 14 with a key connection. FIGS. 7A and 7B illustrate the key connection of the endplate 80 with the first member 12 of the expandable implant 10 more clearly. The rim 88 of the extension 82 is received within the slot portion 66 extending around the perimeter of the first member 12 and second member 14. And the ridge portion 64 of the first member 12 is received within a slot portion of the extension 82. It should be noted that the ridge portion 64, the rim 88 and the slot portion may be configured in various geometrical shapes to operational mate with their opposing feature. When positioning the endplate 80, the endplate is compressed with an instrument and positioned within the hollow portion of the first and/or second member, the endplate 80 is then uncompressed allowing the rim 88 to engage within the slot portion 66 of the first member or second member 12, 14.

FIGS. 8A-8D illustrate yet another embodiment of an endplate suitable for an expandable implant 10. In this embodiment, the endplate 90 includes a plurality of slots 92 positioned around the perimeter of the endplate 90. The endplate 90 may also be configured to be in a wedge-shaped profile to accommodate the natural curvature of the spine. There is also provided a central hollow cavity that is in fluid communication with the hollow cavity of the first member or second member of the implant 10. The endplate 90 has an upper surface 94 and a lower surface 96, the upper surface 94 is configured to engage with bone and the lower surface 96 is provided with connection elements 98 to couple with the first or second member 12, 14 of the expandable implant.

In some embodiments, the plurality of slots 92 may linear, non-linear, or a combination thereof In other embodiments the plurality of slots 92 may be scalloped, grooved, and/or shaped to efficiently allow compression and/or expansion of the endplate. In other embodiments, the endplate 90 may be dimensioned to be in other geometrical shapes such as rectangular, octagonal, spherical, elliptical, and any combination there of. In other embodiments the thickness, width, and length may be varied to provide optimal engagement with the vertebral bodies.

Figure 9:
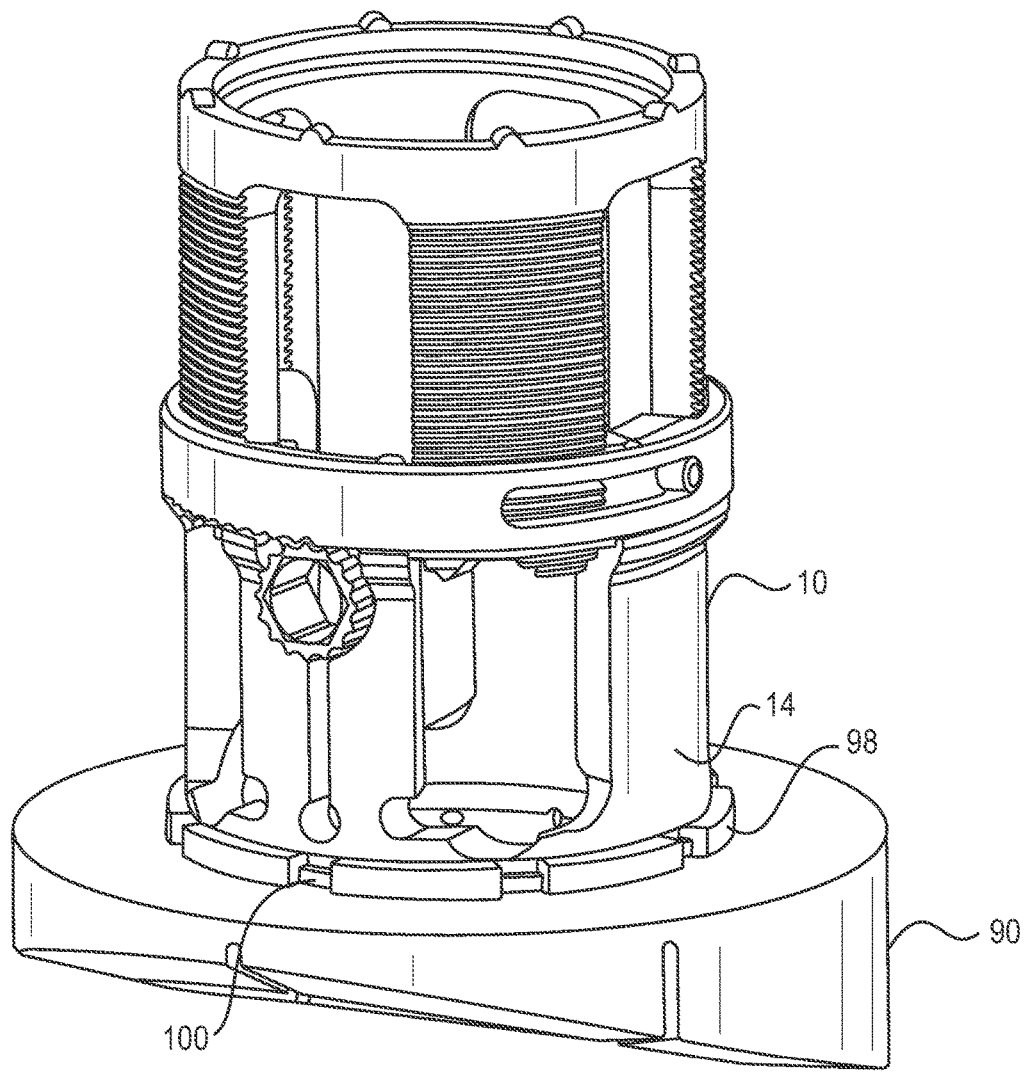
FIG. 9 illustrates the endplate of FIGS. 8A-8D coupled to an expandable implant.

FIG. 9 illustrates the endplate 90 coupled to implant 10. Specifically, endplate 90 is connected to the second member 14 of implant 10. The connection elements 98 couple to a ridge portion 100 of the second member 14.

Figure 10:
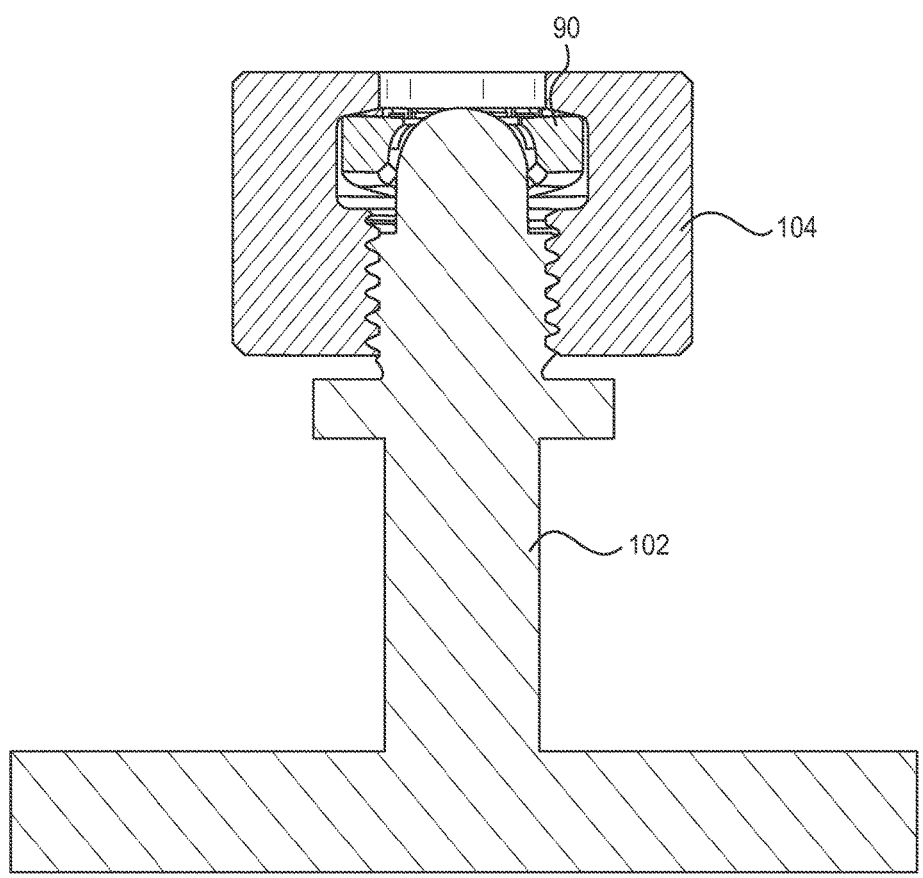
FIG. 10 illustrates the endplate of FIGS. 8A-8D coupled to an instrument for positioning the endplate on the expandable implant.

FIG. 10 illustrates an instrument 102 coupled to the endplate 90 for positioning within the implant 10. The instrument 102 is shown as T-handle type device that is capable of connecting to a housing via a threaded connection. The endplate is positioned in the housing 104 to receive the upper portion of the instrument 102.

Figure 11:
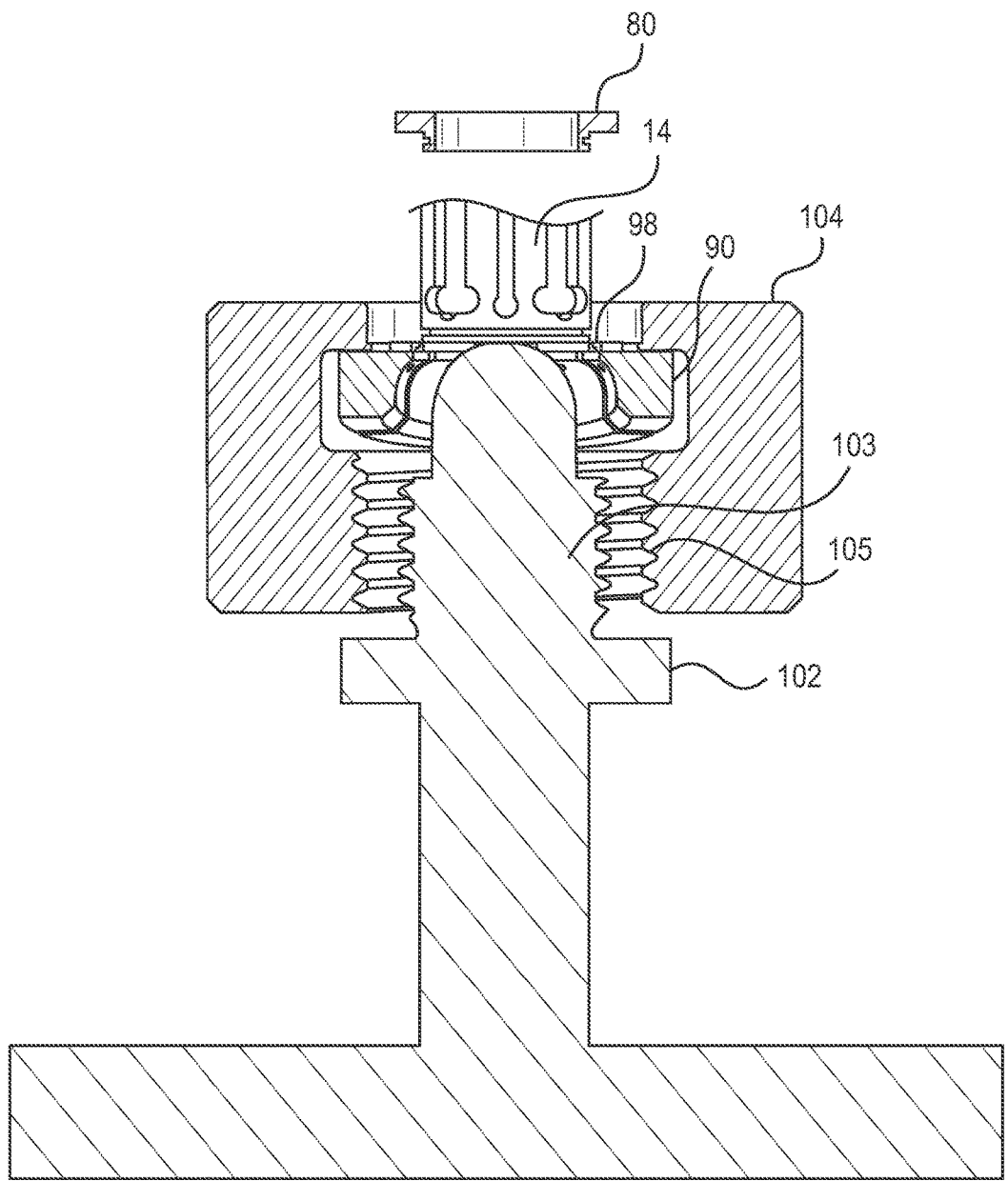
FIG. 11 illustrates another perspective of the instrument and endplate shown in FIG. 10.

FIG. 11 illustrates the instrument 102, endplate 90 and the second member 14 in greater detail. The instrument 102 has a threaded portion 103 that engages with the threaded portion 105 of the housing 104. As the instrument 102 is threaded into the housing 103, the upper portion 105 of the instrument 102 contacts the endplate 90 thereby allowing the endplate to expand. Once the endplate 90 is expanded, the endplate 90 is disengaged from the second member 14. As the instrument 90 is disengaged from the endplate 90, the endplate 90 returns to its original position. When the second member 14 is positioned within the housing 104, and the instrument 12 is disengages from the endplate by unthreading from the housing, the endplate 90 is coupled to the second member 14 through the connection element 98. It should be noted that the housing 104 may be any suitable housing that may receive any geometrical shapes of the endplate. It should also be noted that multiple endplates 90 may be coupled to the first and second members or multiple endplates 80 may be used as well as a combination of endplates 80 and 90. In some embodiments a T-handle type instrument may be used, but in other embodiments any instrument that can apply pressure upon the lower portion of the endplate to expand the endplate may be used.

The dimensions of endplates 80, 90 can be varied to accommodate a patient's anatomy. In some embodiments, the endplates 80, 90 may have any shaped including the wedge-shaped profile to accommodate the natural curvature of the spine. In anatomical terms, the natural curvature of the lumbar spine is referred to as lordosis. When implant 10 is to be used in the lumbar region, the angle formed by the wedge should be approximately between 3.5 degrees and 16 degrees so that the wedge shape is a lordotic shape which mimics the anatomy of the lumbar spine. In alternate embodiments, the wedge shape profile may result from a gradual increase in height from an anterior side to a posterior side to mimic the natural curvature, kyphosis, in other regions of the spine. Thus, in other embodiments, the angle may be between about −4 degrees and −16 degrees.

Although not shown, in one embodiment, bone engaging members may be adapted to be positioned on the bone engaging surfaces of endplates 80, 90. The bone engaging members may comprise conical spikes having a cylindrical base portion. In alternate embodiments, differently shaped bone engaging members may be used, or in other embodiments no bone engaging members may be used. The superior or bone engaging surface of endplate 80 may also include numerous types of texturing to provide better initial stability and/or grasping contact between the end plate and the respective vertebrae. In a preferred embodiment, the texturing may be plurality of teeth. In preferred embodiments where the implant 10 is manufactured from PEEK or other plastic materials, endplates 80, 90 may also include radio-opaque material, such as tantalum markers, which aid in providing location markers in radiographic images.

In preferred embodiments, the length, diameter, and shape of prosthetic device 10 may vary to accommodate different applications, different procedures, implantation into different regions of the spine, or size of vertebral body or bodies being replaced or repaired. For example, implant 10 may be expandable to a longer distance to replace multiple vertebral bodies. Also, endplates 80, 90 can be sized and shaped as well as positioned to accommodate different procedures and approached to the spine. For example, endplates 80, 90 may be made smaller for smaller statured patients or for smaller regions of the cervical spine. In addition, it is not required that endplates 80, 90 be shaped and sized identically and in alternate embodiments they can be shaped or sized differently than each other and/or include different bone engaging members or texturing.

Depending on the orientation and positioning of the implant 10, the endplates 80, 90 may be provided with a certain degree of lordosis or kyphosis to mimic a natural or unnatural curvature of the spine. In order to facilitate the proper alignment of the implant 10, endplates 80, 90 may be provided with a first series of markings and endplate 90 may be provided with a corresponding second series of markings. When at least one of the first and second series of markings are aligned, the first and second endplates are aligned for a specific approach to the spine (e.g., anterior implantation) and to provide the desired lordosis or kyphosis. The marking scheme (e.g., numbering scheme) aids in assembly of the endplates to the other components of the implant by allowing a user to align the markings for varying approaches to the spine.

The first and second series of markings may include characters, alphanumeric characters, numeric characters, colors, symbols, shapes, words, pictures, or similar indicia. These markings may be etched, engraved, or otherwise marked or applied on the endplates. The first series of markings preferably includes a plurality of different markings. In other words, the first series of markings preferably includes a plurality of markings that do not repeat and are not the same.

Similarly, the second series of markings preferably includes a plurality of different markings which correspond to the first series of markings. When one of the first series of markings is aligned with the one of the second series of markings, the endplates are positioned and aligned for a given implantation approach.

While the invention herein disclosed has been described by means of specific embodiments and applications thereof, numerous modifications and variations can be made thereto by those skilled in the art without departing from the scope of the invention as set forth in the claims.

What is claimed is:

1. An expandable prosthetic implant for engagement between vertebrae, comprising:
   a first member having a first end, a second end, a plurality of extensions and and a hollow interior portion extending from the first end to the second end, wherein the plurality of extensions extend from the first end to the second end,
   a second member having a first end, a second end, a hollow interior portion extending from the first end to the second end, and a plurality of extensions extending from the second end to the first end, and wherein the first member is moveable relative to the second member along a longitudinal axis;

a ring positioned coaxial to the first member and the second member and axially fixed to the second member; and an actuator coupled to the second member and operationally coupled to the ring for locking the first member to the second member, wherein the ring is configured to be rotated from a first position to a second position by rotation of the actuator, and wherein in the first position, the first member is freely moveable with respect to the second member and in a second position, the first member is locked in a position with respect to the second member.

2. The implant of claim 1, wherein the first member and the second member include surfaces having a plurality of spaced apart endplate engagement features for coupling to a first and second endplates.

3. The implant of claim 1, wherein the second member includes a first opening and a second opening for a receiving a first pin and a second pin, the first and second pin configured to couple the ring to the second member.

4. The implant of claim 3, wherein the ring includes a slot extending on the perimeter of outer surface of the ring and configured to receive a first or second pin.

5. The implant of claim 1, wherein the ring includes an inner surface and an outer surface, the inner surface further including spaced apart engagement portions for engaging with the engagement features of at least one of the plurality of extensions of the first member.

6. The implant of claim 1, wherein the ring includes a marking to visual gauge the first position and the second position.

7. The implant of claim 1, wherein the actuator is positioned within one of the plurality of extension of the second member.

8. The implant of claim 1, wherein the plurality of extensions of the second member have an outer surface that includes a ledge that is configured to receive the ring.

9. An expandable prosthetic implant for engagement between vertebrae, comprising:
- a first member having a first end, a second end, a plurality of extensions and a hollow interior portion extending from the first end to the second end, wherein the plurality of extensions extend from the first end to the second end,
- a second member having a first end, a second end, a hollow interior portion extending from the first end to the second end, and a plurality of extensions extending from the second end to the first end, and wherein the first member is moveable relative to the second member along a longitudinal axis; and
- an actuator coupled to one of the plurality of extensions of the second member;
- wherein at least one of the plurality of extension of the first member includes engagement features for couple with the corresponding engagement element configured on side surfaces of the one of the plurality of extensions of the second member,
- wherein when the actuator is rotated from a first position to a second position, the one of the plurality of extensions flexes out, whereby the engagement features of the first member engages with the engagement element of the one of the plurality of extensions of the second member thereby locking the first member with respect to the second member, and
- wherein in the first position, the first member is freely moveable with respect to the second member and in a second position, the first member is locked in a position with respect to the second member.

10. The implant of claim 9, wherein the actuator is positioned within one of the plurality of extension of the second member.

11. The implant of claim 9, wherein the one of the plurality of extensions of the second member includes a housing for receiving the actuator.

12. The implant of claim 11, wherein the one of the plurality of extensions includes a slot that extends from the housing to the second end of the second member.

13. The implant of claim 9 wherein the one of the plurality of extensions is configured to flex.

14. The implant of claim 9, wherein the engagement features and engagement element are one of non-helical threads, tabs, teeth, and protrusions.

15. The implant of claim 9, wherein an instrument is used to move the first member relative to the second member.

16. The implant of claim 9, wherein the first member and the second member include endplate engagement features for engaging with a first and a second endplate.

17. An expandable prosthetic implant for engagement between vertebrae, comprising:
- a first member having a first end, a second end, a plurality of extensions and and a hollow interior portion extending from the first end to the second end, wherein the plurality of extensions extend from the first end to the second end;
- a second member having a first end, a second end, a hollow interior portion extending from the first end to the second end, and a plurality of extensions extending from the second end to the first end, and wherein the first member is moveable relative to the second member along a longitudinal axis; and
- an endplate having a plurality of slots and being configured to be compressible,
- wherein the endplate includes an upper surface for engaging with a vertebral body, and an extension portion having an engagement element that engages with endplate engagement features of the first or second members.

18. The implant of claim 17, wherein the endplate further includes the engagement element is a rim.

19. The implant of claim 17, wherein the engagement element is a plurality of connection elements spaced apart on a bottom surface of the endplate.

20. The implant of claim 17, wherein an instrument is used to position the endplate.

* * * * *